United States Patent
Schwahn et al.

(10) Patent No.: US 6,777,503 B2
(45) Date of Patent: Aug. 17, 2004

(54) METHOD FOR HYDROFORMYLATING OLEFINS HAVING BETWEEN 20 AND 400 CARBON ATOMS

(75) Inventors: Harald Schwahn, Wiesloch (DE); Gerhard Borchert, Ludwigshafen (DE); Klaus Diehl, Hassloch (DE); Armin Volker Grenacher, Mutterstadt (DE); Friedrich Sauer, Obersülzen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 195 days.

(21) Appl. No.: 10/181,454
(22) PCT Filed: Jan. 26, 2001
(86) PCT No.: PCT/EP01/00853
§ 371 (c)(1), (2), (4) Date: Jul. 18, 2002
(87) PCT Pub. No.: WO01/55068
PCT Pub. Date: Aug. 2, 2001

(65) Prior Publication Data
US 2003/0013819 A1 Jan. 16, 2003

(30) Foreign Application Priority Data
Jan. 28, 2000 (DE) .......................................... 100 03 871

(51) Int. Cl.$^7$ ................................................. C08F 10/00
(52) U.S. Cl. ....................................................... 525/333.7
(58) Field of Search ........................................ 525/333.7

(56) References Cited

U.S. PATENT DOCUMENTS

3,488,184 A    1/1970  Hesler
4,419,195 A  * 12/1983  Young ........................ 205/457

FOREIGN PATENT DOCUMENTS

GB    1132666    11/1968
WO    98/12235    3/1998

OTHER PUBLICATIONS

Encyclopedia of Chemical Processing and Design, 17, pp. 223–251.
Auslegungskriterien fur elektrostatische emulsionsspaltanlagen, Draxler et al., 525–530.

* cited by examiner

Primary Examiner—William Cheung
(74) Attorney, Agent, or Firm—Keil & Weinkauf

(57) ABSTRACT

A process for the hydroformylation of olefins having from 20 to 400 carbon atoms by reaction of the olefins with synthesis gas in the presence of a cobalt carbonyl catalyst and recovery of the cobalt catalyst by extraction of the reaction product with an aqueous acidic solution in the presence of oxygen and separation of the organic and aqueous phases, wherein (a) the aqueous phase is separated from the organic phase by means of gravitational forces to the extent that the proportion of aqueous phase dispersed in the organic phase is 2% by weight or less, based on the organic phase, and (b) the organic phase obtained in step (a) is exposed to an electric field to coalesce the remaining dispersed aqueous phase, is described.

In this way, the residual cobalt content of the hydroformylation product can be reduced to less than 1 ppm.

10 Claims, 1 Drawing Sheet

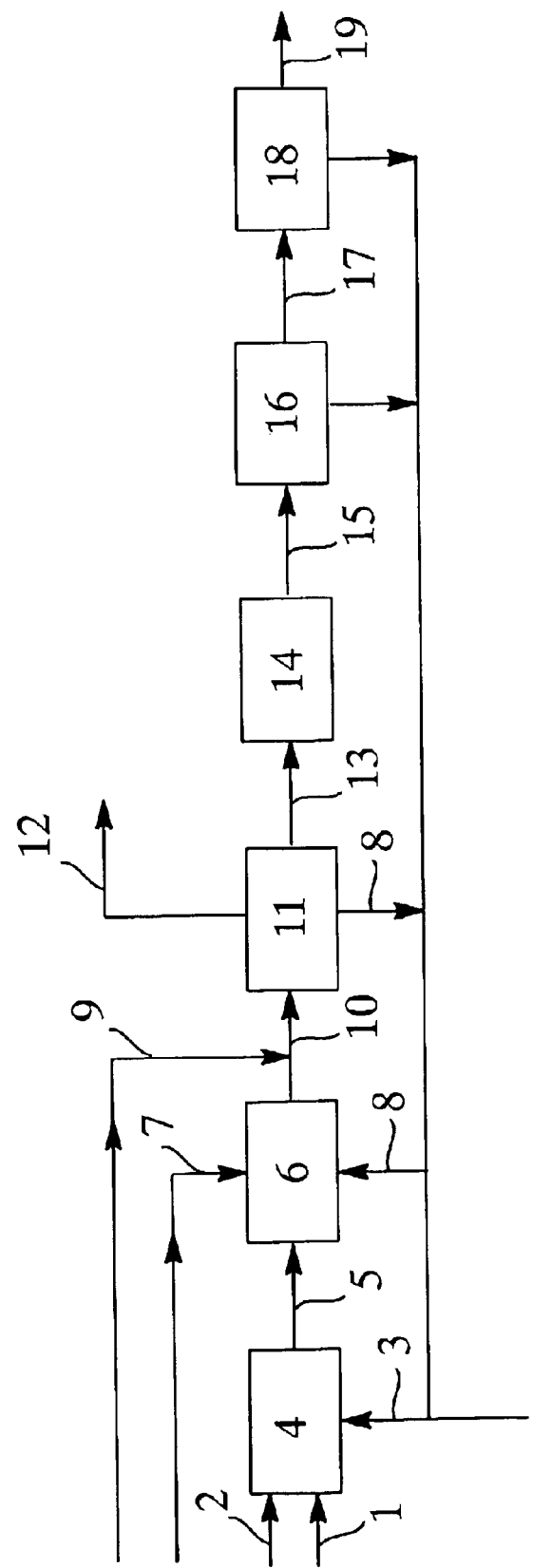

METHOD FOR HYDROFORMYLATING OLEFINS HAVING BETWEEN 20 AND 400 CARBON ATOMS

The present invention relates to a process for the hydroformylation of olefins having from 20 to 400 carbon atoms by reaction of the olefins with synthesis gas in the presence of a cobalt carbonyl catalyst.

Hydroformylation, also known as the oxo process, is a process which has been carried out on an industrial scale for decades. In this process, olefins are reacted with mixtures of carbon monoxide and hydrogen in the presence of carbonyl complexes of metals of transition group VIII of the Periodic Table, in particular those of cobalt or rhodium, to produce aldehydes which have one more carbon atom (cf. the monograph "New Syntheses with Carbon Monoxide", J. Falbe (editor), Springer Verlag 1980.

At present, cobalt is used virtually exclusively as catalytically active metal for the hydroformylation of relatively long-chain olefins. The known process variants of the cobalt-catalyzed hydroformylation differ, in particular, in the way in which the catalyst which is homogeneously dissolved in the reaction mixture is separated from the reaction products. For economic reasons and to free the hydroformylation product of catalyst, this has to be separated off as completely as possible and returned to the synthesis step. An elegant way of separating of the catalyst is to make the homogeneously dissolved catalyst heterogeneous in a liquid phase which is immiscible with the hydroformylation product.

For this purpose, it is customary, as described in DE-A-2404855, to treat the reaction mixture with molecular oxygen in the presence of aqueous acid. The cobalt is oxidized from the oxidation state −1 to +2 and can then be removed by extraction with the aqueous solution. The aqueous extract is separated off, for example, by decantation in a phase separation vessel or in other apparatuses suitable for this purpose.

In the hydroformylation of short-chain olefins, the residual amount of cobalt remaining in the organic phase is usually less than about 2 ppm. As the chain length of the aldehyde/alcohol mixtures produced increases, i.e. at a number of carbon atoms of more than 12, the surface-active properties of the reaction products increase. This results in the finely dispersed liquid-liquid-gas dispersion which is initially formed in the cobalt removal step being stabilized and the droplet-droplet coalescence or droplet-interface coalescence being inhibited.

Only after relatively long residence times does the emulsion break up substantially into the two liquid, each homogeneous phases.

DE-AS-1285997 and U.S. Pat. No. 3,488,184 describe the removal of cobalt(II) salts from the reaction products of the oxo process by means of cation exchangers. Disadvantages in long-term industrial use are the swelling behavior of many ion-exchange resins in the presence of the aldehyde-containing reaction product and the complicated regeneration of the ion-exchange resins.

A particularly interesting application of the hydroformylation reaction using a cobalt catalyst is, according to EP-A-244616, the hydroformylation of polybutenes or polyisobutenes to give polybutyl or polyisobutyl aldehydes, alcohols or esters.

Due to the high viscosity and the surface-active properties of the oxo products of poly(iso)butenes, effective removal of the cobalt catalyst used can be achieved only with difficulty. In the oxidative decomposition of the cobalt carbonyls present in the output from the reactor in the presence of an acidic aqueous solution, extremely stable water-in-oil emulsions are formed. Phase separation on the basis of the density difference requires very long residence times, as a result of which economical separation under the earth's gravity is not possible.

WO 98/12235 describes the combined use of polymeric emulsion breakers and coalescence-promoting apparatuses in order to accelerate the phase separation of reaction products from the hydroformylation of olefins having from 12 to 100 carbon atoms. While this procedure succeeds in reducing the residual cobalt content of the $C_{12}$–$C_{18}$-olefins in the hydroformylation products to below 1 ppm, a residual cobalt content of from 6 to 9 ppm remains in (iso)butene oligomers having 20 carbon atoms or more formed as oxo products. These residual amounts of cobalt can have an adverse effect in the further processing of the hydroformylation products. Both in the work-up by distillation and in chemical reactions in the presence of hydrogen, e.g. hydrogenation or hydrogenative amination, solid deposits of cobalt salts or metallic cobalt can form in the apparatuses, and these impair mass and/or heat transfer. The deposits have to be removed periodically by mechanical or chemical means, e.g. by dissolution in nitric acid. These necessary measures are inconvenient and adversely affect the economics of the further processing steps.

WO 98/12235 points out the possibility of separating the finely dispersed residual water from the organic phase by means of electrostatic coalescence apparatuses in place of mechanical coalescence apparatuses.

Such electrostatic coalescence apparatuses have already been used in petroleum recovery for separating off salt-containing water which originates from the oil reservoirs and is present in emulsified form in the crude oil, cf., for example, "Encyclopedia of Chemical Processing and Design", Vol. 17, p. 223, New York 1983; and Chem.-Ing.-Techn. 62 (1990), No. 7, p. 525. In the first literature reference, it is stated on p. 224 that: "all [electric] desalinators require the addition of washing water, usually in the range from 4 to 8% by volume, based on the crude input."

It has been found that when an attempt is made to use an electrostatic coalescence apparatus for separating the organic phase, which still contains, for example, up to 5% by weight of water, obtained after aqueous work-up of a reaction product from the hydroformylation of poly(iso)butenes and subsequent phase separation, short circuits and deposition of metallic cobalt are observed, which is a drawback. This phenomenon is presumably due to the high electrical conductivity of the aqueous phase owing to the presence of dissolved cobalt(II) salts and the tendency of the emulsified water droplets to form string-of-beads-type aggregates in the field direction and the comparative ease of reduction of the cobalt(II) salts to metallic cobalt. These problems appear to be inherent in the system, and an obvious solution was not able to be found.

It is an object of the present invention to purify reaction products from the cobalt-catalyzed hydroformylation of olefins having from 20 to 400 carbon atoms to residual cobalt contents of 2 ppm or less, in particular 1 ppm or less, and to provide an efficient process for this purpose which is reliable in long-term industrial operation.

We have found that this object is achieved by a process for the hydroformylation of olefins having from 20 to 400 carbon atoms by reaction of the olefins with synthesis gas in the presence of a cobalt carbonyl catalyst and recovery of the cobalt catalyst by extraction of the reaction product with an aqueous acidic solution in the presence of oxygen and separation of the organic and aqueous phases, wherein (a) the aqueous phase is separated from the organic phase by means of gravitational forces to the extent that the proportion of aqueous phase dispersed in the organic phase is 2% by weight or less, based on the organic phase,
(b) the organic phase obtained in step (a) is exposed to an electric field to coalesce the remaining dispersed aqueous phase.

In the process of the present invention, it is critical that the content of dispersed aqueous phase is reduced to 2% by weight or less, preferably 1% by weight or less, in particular 0.5% by weight or less, before the organic phase is passed to an electrocoalescence apparatus. No water is added to the organic phase which has been freed of the major part of the aqueous phase in this way. This finding is surprising, since it is contrary to the express advice in the prior art (cf. "Encyclopedia of Chemical Processing and Design" above, Vol. 17), according to which from 4 to 8% by volume of washing water should be added to the crude emulsion to be broken in the removal of salt solutions from oil by means of electrocoalescence.

The hydroformylation is carried out in a manner known per se. It is appropriately carried out at pressures of from 100 to 400 bar and at a temperature of from 100 to 200° C. The synthesis gas comprises carbon monoxide and hydrogen, generally in a ratio of from 1:10 to 10:1. The cobalt carbonyl catalyst is advantageously formed in situ in the hydroformylation reactor from an aqueous cobalt(II) salt solution, e.g. cobalt(II) formate or acetate solution.

As olefins to be hydroformylated, it is possible to use those having from 20 to 400 carbon atoms, in particular polyalkenes, i.e. oligomers or polymers of $C_2$–$C_6$-alkenes, with the oligomers or polymers being olefinically unsaturated. In particular, polyisobutenes, preferably polyisobutenes having a predominantly terminal double bond, as are disclosed, for example, in U.S. Pat. No. 5,286,823, can be employed.

If desired, inert organic diluents such as saturated aliphatic hydrocarbons or aromatic hydrocarbons can be additionally used to lower the viscosity.

The reaction product from the hydroformylation is appropriately let down to intermediate pressure, generally from 10 to 30 bar, after leaving the reaction zone and is passed to the decobalting stage. In the decobalting stage, the reaction mixture is freed of cobalt carbonyl complexes in the presence of an aqueous, slightly acidic solution, e.g. having a pH of from 2 to 6, using air or oxygen at temperatures of preferably from 90 to 130° C. Decobalting can, if desired, be carried out in a pressure vessel packed with packing elements, e.g. Raschig rings, so as to produce a very high mass transfer area.

According to the present invention, the aqueous phase is separated from the resulting mixture of aqueous phase and organic phase by means of gravitational forces to the extent that the proportion of dispersed aqueous phase is 2% by weight or less, preferably 1% by weight or less, in particular 0.5% by weight or less.

Separation techniques utilizing gravitational forces include settling, centrifugation and mechanical coalescence stages and combinations thereof. Most preferred is a combination of (i) settling and/or centrifugation and (ii) one or more mechanical coalescence stages. In general, substantial separation of the aqueous phase is achieved first by settling and/or centrifugation to give a fine emulsion which no longer demixes spontaneously and usually still contains more than 2–5% by weight of aqueous phase.

To allow it to settle, the mixture of aqueous and organic phases can be introduced into a calming zone and be separated there. This is advantageously achieved in a horizontal, continuously operated phase separation vessel through which the mixture flows at a low flow velocity. Due to the density difference between the phases, the emulsion separates in the earth's gravitational field, so that the two phases are obtained above one another in cohesive form and largely free of extraneous phase. The aqueous phase obtained is virtually free of organic phase, so that the cobalt salt solution can be returned without further work-up to the decobalting stage.

Before the organic phase, which is obtained as a fine emulsion, can be passed to coalescence in the electric field, the residual content of dispersed aqueous phase has to be reduced to 2% by weight or less. For this, it is advantageous to use one or more mechanical coalescence stages with an integrated or downstream phase separation apparatus. Separators having coalescence internals such as packing elements, coalescence surfaces or fine-pored elements are generally suitable.

The coalescence surface internals are generally plate packs having corrugated or inclined surfaces on which dispersed droplets deposit and initially form a film. When this film surrounds the individual plate and is thick enough, large droplets of dispersed phase are formed at the edge of the plate and fall downward. They then form a layer in the separator which can be separated off easily by mechanical means.

In the case of fine-pored internals, the internal structure of the elements forces the finely dispersed droplets into contact with the internal surface so that they form a film and leave the hollow structure of the fine-pored elements as larger coalesced droplets.

Suitable packing elements are the packing elements customarily used in distillation. Preferably, the fine dispersion is conveyed from the top downward through a bed of packing. Wetting of the large area of the packing leads to surface coalescence and simultaneously by means of droplet motion to droplet-droplet coalescence. In an advantageous embodiment, use is made of a vertical packed column in which the packing elements are made of a material which is wetted by the disperse aqueous phase and the bed of packing is flooded by the organic phase. Preference is given to using packed columns filled with packing elements made of metal, e.g. metal rings. The large droplets of aqueous phase which form separate out rapidly and can be taken off as a lower phase. The hydroformylation product is taken off above the phase separation interface.

After the (last) mechanical coalescence stage, the organic phase contains 2% by weight or less, preferably 1% by weight or less, in particular 0.5% by weight or less, e.g. from 0.05 to 0.3% by weight, of dispersed aqueous phase in the form of a very fine emulsion.

In order to obtain an advantageous viscosity of the hydroformylation product during the separation of the aqueous phase by means of gravitational forces, in particular in the preferred mechanical coalescence stage, a temperature of from 50 to 120° C. is advantageously maintained. Adherence to a temperature in the given range is also advantageous in the electrocoalescence stage.

Additional use of emulsion breakers is advantageous in the phase separation, in particular in the separation of the aqueous phase by means of gravitational forces. Suitable emulsion breakers are, in particular, alkoxylated compounds as are customarily used in the petroleum industry for separating off the salt-containing water. These are, for example, (a) oligoamines, polyamines, oligoimines and polyimines alkoxylated with propylene oxide and, if desired, additionally ethylene oxide, and
(b) alkoxylated alkylphenol-formaldehyde resins and
(c) ethylene oxide-propylene oxide block copolymers and also
(d) their polymeric acrylic esters, as are described in DE-A-2227546 and DE-A-2435713 (a); DE-A-2013820 (b); DE-A-1545215 (c) and DE-A-4326772 (d).

Particular preference is given to using an emulsion breaker which is obtained by reaction of polyethylenimine having a molecular weight of from 10,000 to 50,000 with such amounts of propylene oxide and, if desired, additionally ethylene oxide that the content of alkoxy units is from 90 to 99% by weight.

The amount of emulsion breakers added to achieve the desired effect is from about 0.1 to 100 g/t of organic material used, preferably from 2 to 20 g/t.

The emulsion breaker is preferably added continuously in diluted form. Dilution with an inert solvent, e.g. o-xylene, aids handling and also aids metering of the small amount required. It is advantageously added after decobalting, preferably together with the addition of the aqueous extraction solution and the air during depressurization, as a result of which the emulsion breaker is effectively mixed in.

The organic phase which has been freed of the major part of the aqueous phase using gravitational forces is subsequently exposed to an electric field to induce droplet-droplet coalescence of the dispersed droplets of residual aqueous phase. The coalesced aqueous phase can then be separated off in an integrated or downstream phase separation apparatus. To achieve the coalescence in the electric field, it is in principle possible to use any arrangement of two electrodes between which the very fine emulsion of organic phase and residual dispersed aqueous phase can be introduced. Customary construction types are (a) petroleum breakers which have a metal electrode and in which the aqueous phase which has already coalesced acts as second electrode, so that the electric field acts between the metal electrode and the interface,
(b) annular breakers which have two concentric electrodes and in which the inner electrode is usually a rod electrode;
(c) plate breakers in which the electrodes are configured as parallel plates.

Annular breakers, in particular those in which the outer electrode is located at a distance of about 100 mm around an inner electrode configured as a rod electrode, have been found to be particularly useful.

It is possible to employ a DC voltage or an AC voltage. Suitable DC voltages are from 5 to 40 kV, preferably from 10 to 40 kV. Suitable AC voltages are from 0.5 to 20 kV, preferably from 3 to 5 kV, at frequencies of from 50 to 20,000 Hz.

The electric field generated is preferably inhomogeneous. Furthermore, the electric field direction is preferably perpendicular to the force of gravity.

In the breaking of the emulsion in the electric field, an increase in the coalescence rate is produced by an electrically induced motion of the droplets. In an inhomogeneous electric field, the droplets do not move to the electrodes, but rather in the direction of higher field strength. The larger droplets formed by coalescence can then settle more quickly in the direction of the earth's gravity.

The treatment in the electric field can remove the aqueous phase to values corresponding to the solubility of the aqueous phase in the hydroformylation product. In this way, the residual cobalt content can be reduced to values of 2 ppm or less, usually 1 ppm or less, preferably 0.8 ppm or less.

DESCRIPTIONS OF THE DRAWINGS

An advantageous embodiment of the process of the present invention is described in detail below with the aid of the attached schematic drawing:

Via the lines (1) to (3), olefin (1) and synthesis gas (oxo gas) (2) and an aqueous cobalt salt solution (3) are fed to the hydroformylation reactor (4). In the reactor (4), the reaction with oxo gas takes place under customary hydroformylation conditions to give the oxygen-containing compounds. The product mixture comprising the active catalyst in the form of the hydridocobalt carbonyl is passed via line (5) to the decobalting stage (6) and is there treated with air via line (7) and an aqueous acidic cobalt salt solution (8). Here, the cobalt changes its oxidation state from −1 to +2 and is dissolved as cobalt salt in the acidic aqueous phase. Immediately after decobalting, an emulsion breaker is added via line (9) and the crude reaction product is conveyed via line (10) to a phase separation vessel (11). Here, the gas phase and the two liquid phases separate to a substantial extent. The unreacted air and the entrained CO and $H_2$ from the synthesis stage are discharged via line (12).

After the phase separation (11), the organic phase containing a small amount of the aqueous phase is conveyed via line (13) to a mechanical coalescence stage (14), preferably a packed column filled with metal packing elements, e.g. Pall rings. In the downstream phase separation vessel (16), to which the organic phase goes via line (15), the droplets of aqueous phase which have been enlarged by coalescence settle out and are separated off.

The mechanical coalescence stage is followed, via line (17), by an electric coalescence stage (18) in which the finely dispersed aqueous phase is exposed to an electric field. The droplets of aqueous phase which have been enlarged by coalescence are completely separated off so as to give a virtually cobalt-free product which can be worked up in a customary manner.

The aqueous phase (8) separated off in the stages (11), (16) and (18) is partly recirculated to the decobalting stage (6) and partly to the hydroformylation reactor (4).

The process of the present invention is illustrated by the following examples.

EXAMPLES

Example 1 (Comparative, Not According to the Present Invention)

3660 kg/h of a mixture of 1940 kg/h of polyisobutenes (MN about 1000) and 1720 kg/h of a $C_{10}$–$C_{14}$-paraffin hydrocarbon fraction and also 300 kg/h of an aqueous acidic cobalt formate solution containing 1.3% by weight of cobalt were introduced into a hydroformylation reactor. The mixture was reacted at 183–185° C. with a $CO/H_2$ mixture (40% by volume of CO; 59.5% by volume of $H_2$; 0.5% by volume of inerts). To maintain a total pressure of 275 bar, fresh gas of the abovementioned composition was continually fed to the reactor via a pressure regulator.

After passing through the reaction zone, the product was depressurized into a decobalting stage, with the pressure being reduced to about 20 bar. At the same time, 2600 kg/h of cobalt formate solution of the abovementioned composition together with 17 kg/h of air were introduced into the decobalting zone. Immediately downstream of the outlet from the decobalting stage, an emulsion breaker was added as a dilute solution in such an amount that the concentration was 12 g/t of reaction product. The emulsion breaker employed was a polyethylenimine modified with propylene oxide (molecular weight of the polyethylenimine used for its preparation: about 20,000; content of propoxy units: 99% by weight).

The combined streams from the decobalting stage passed through a mixing section and then went into a phase separation vessel from which 200 kg/h of depressurization gas were discharged into a collection system. The liquid phases separated to a substantial extent. The aqueous cobalt formate solution was virtually free of organics and was recirculated partly to the decobalting stage and partly to the reactor.

The organic phase still contained about 0.7% by weight of emulsified cobalt formate solution. To decrease the content of cobalt formate solution, the reaction product was cooled to 80° C. and passed from the top downward through a vertical packed column (length: 6.5 m, diameter: 0.7 m). An aqueous cobalt formate solution settled below the bed of packing and was returned to the process, while the organic phase was taken off above the interface. The slightly turbid organic phase still contained 0.14% by weight of water and 8 ppm of cobalt. The method of determining cobalt is indicated below.

Example 2 (According to the Present Invention)

330 kg/h of the slightly turbid organic phase taken off from the packed column as described in Example 1 were branched off via the bypass and fed at 70° C. to a vertical cell of a commercial Metercell® precipitator from Petrolite Corp., Houston, Tex., which is fitted with a concentric, uninsulated rod electrode and is capable of scale-up. The precipitator was under a pressure of 1.1 bar and the throughput per cross-sectional area was about 13.5 m³/m²×h. The cell was operated at a DC voltage of 40 kV, and the current drawn was less than 5 mA. The organic phase coming from the Metercell® precipitator was, in contrast to the main stream, completely clear and had a residual water content corresponding to the solubility at 70° C. of 0.06% by weight. The cobalt content had dropped to below 1 ppm. At the bottom of the cell, about 250 ml/h of aqueous phase containing 1.3% by weight of cobalt salt (calculated as Co) separated out.

Example 3 (According to the Present Invention)

100 ml of the slightly turbid organic phase taken off from the packed column as described in Example 1 were placed in the cell of a heatable, laboratory electrostatic precipitator. The precipitator was equipped with two concentric electrodes, with the inner electrode being configured as a metal rod electrode (diameter: 8 mm) and the outer electrode being formed by an electrolyte solution (salt solution) which was present in the annular space and was insulated by means of the glass wall (glass tube internal diameter: 20 mm). The precipitator was heated to 70° C. by means of heating medium circulating through a further annular space. Since the precipitator was made of glass, the separation process could be observed very well. On application of an AC voltage of 4 kV (50 Hz), complete separation of the disperse aqueous phase containing cobalt salt occurred within 10 seconds. In contrast to the original sample, the organic phase was completely clear and had, at 70° C., a residual water content of 0.06% by weight, which corresponds to the solubility. The cobalt content of the clear organic phase was less than 1 ppm. The pink aqueous phase containing cobalt salt had separated out at the bottom of the cell.

Method of Determining Cobalt by Mass Spectrometry

About 2 g of the sample are subjected to an automated digestion process (firstly cracking with 10 ml of sulfuric acid at about 320° C.; then decomposition of the residue using 8 ml of mixed acid at about 160° C.) in which the organic components of the sample are cracked and completely oxidized by means of hot, concentrated mineral acids. After fuming off the mineral acids, the cobalt remains in hydrochloric acid solution. The digestion solution is adjusted to 25 ml. The cobalt content of this solution is determined by mass spectrometry combined with inductively coupled plasma (ICP-MS).

The following reagents are used:

| Twice-distilled or deionized water | |
|---|---|
| Sulfuric acid, $\beta(H_2SO_4)$ | about 1.84 g/ml |
| Hydrochloric acid, $c(HCl)$ | about 5 mol/l |
| Nitric acid, $\beta(HNO_3)$ | about 1.41 g/ml |
| Perchloric acid, $\beta(HClO_4)$ | about 1.67 g/ml |

Mixed acid: a mixture of nitric acid, sulfuric acid and perchloric acid in a volume ratio of 2:1:1.

Apparatus:

ICP-MS spectrometer, e.g. Perkin Elmer "Elan 5000"

| Measurement conditions: | Atomizer: | crossflow |
|---|---|---|
| | Generator: | 1050 W |
| | Measurement time: | 1.5 s |
| | Mass: | 59 |

We claim:

1. A process for the hydroformylation of olefins having from 20 to 400 carbon atoms by reaction of the olefins with synthesis gas in the presence of a cobalt carbonyl catalyst and recovery of the cobalt catalyst by extraction of the reaction product with an aqueous acidic solution in the presence of oxygen and separation of the organic and aqueous phases, wherein (a) the aqueous phase is separated from the organic phase by means of gravitational forces to the extent that the proportion of aqueous phase dispersed in the organic phase is 2% by weight or less, based on the organic phase, and (b) the organic phase obtained in step (a) is exposed to an electric field to coalesce the remaining dispersed aqueous phase.

2. A process as claimed in claim 1, wherein an inhomogeneous electric field is used.

3. A process as claimed in claim 1, wherein a DC field having a voltage of from 5 to 40 kV is used.

4. A process as claimed in claim 1, wherein an AC field having a voltage of from 0.5 to 20 kV and a frequency of from 50 to 20,000 Hz is used.

5. A process as claimed in claim 1, wherein the phase separation is carried out in the presence of an emulsion breaker.

6. A process as claimed in claim 5, wherein the emulsion breaker used is a polyethylenimine alkoxylated with propylene oxide and/or ethylene oxide.

7. A process as claimed in claim 1, wherein the step (a) comprises a mechanical coalescence stage.

8. A process as claimed in claim 7, wherein the mechanical coalescence stage used is a vertical packed column in which the packing elements are made of a material which is wetted by the disperse aqueous phase and the bed of packing is flooded by the organic phase.

9. A process as claimed in claim 1, wherein a temperature of from 50 to 120° C. is maintained in steps (a) and/or (b).

10. A process as claimed in claim 1, wherein the olefin used is polyisobutene.

* * * * *